United States Patent [19]

Sauers

[11] 4,228,109
[45] Oct. 14, 1980

[54] 1-ALKYL-2,2-DICHLORO-2(PHOSPHINYL-)ACETATES

[75] Inventor: Richard F. Sauers, Hockessin, Del.

[73] Assignee: E. I. Du Pont de Nemours and Company, Wilmington, Del.

[21] Appl. No.: 930,599

[22] Filed: Aug. 1, 1978

Related U.S. Application Data

[63] Continuation-in-part of Ser. No. 914,756, Jun. 14, 1978, abandoned, which is a continuation-in-part of Ser. No. 828,213, Aug. 26, 1977, abandoned.

[51] Int. Cl.$^2$ .......................... A01N 9/36; C07F 9/40
[52] U.S. Cl. ..................................... 260/941; 260/937; 260/326.2; 260/936; 544/157; 544/337; 546/21; 560/105; 560/226; 71/86; 71/87
[58] Field of Search ........................... 260/941; 71/86; 560/105, 226

[56] References Cited

U.S. PATENT DOCUMENTS

| 2,830,927 | 4/1958 | Sallmann | 260/941 UX |
| 2,831,014 | 4/1958 | Sallmann et al. | 260/941 |
| 2,861,914 | 11/1958 | Sallmann | 260/941 UX |
| 2,995,486 | 8/1961 | Sallmann | 260/941 UX |
| 3,624,188 | 11/1971 | Curry | 260/941 UX |
| 3,627,842 | 12/1971 | Nicholson | 260/941 UX |
| 3,649,722 | 3/1972 | Nicholson | 260/941 |
| 3,772,412 | 11/1973 | Quimby et al. | 260/932 |
| 3,776,984 | 12/1973 | Ratts | 260/941 X |
| 4,042,650 | 8/1977 | McIntosh | 71/86 |

FOREIGN PATENT DOCUMENTS

| 593264 | 2/1960 | Canada | 260/941 |
| 300840 | 8/1954 | Switzerland | 260/941 |
| 304272 | 12/1954 | Switzerland | 260/941 |
| 310406 | 12/1955 | Switzerland | 260/941 |
| 310408 | 12/1955 | Switzerland | 260/941 |
| 310410 | 12/1955 | Switzerland | 260/941 |
| 310412 | 12/1955 | Switzerland | 260/941 |

OTHER PUBLICATIONS

English translation of French Patent 1,110,787, to Geigy, published 2/1956.
Abstract of Japanese Application J52064-429.
Lichtenthaler, "Chemical Reviews", vol. 61, (1961) pp. 607 to 649.

*Primary Examiner*—Anton H. Sutto

[57] ABSTRACT

This invention relates to aliphatic phosphorous containing compounds which are useful as herbicides. Additionally, they demonstrate tolerance towards desired, crops, e.g. wheat and rice.

10 Claims, No Drawings

1-ALKYL-2,2-DICHLORO-2(PHOSPHINYL)ACETATES

RELATED APPLICATIONS

This application is a continuation-in-part of my copending application U.S. Ser. No. 914,756 filed June 14, 1978 which is a continuation-in-part of my application U.S. Ser. No. 828,213 filed Aug. 26, 1977, both now abandoned.

BACKGROUND OF THE INVENTION

In U.S. Pat. No. 2,995,486 compounds such as

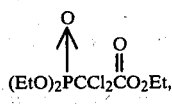
(EtO)$_2$PCCl$_2$CO$_2$Et, are taught to be useful as insecticides.

Numerous compounds have been disclosed within recent years which are active herbicides; the need still exists, however, for herbicides which are more active. The presence of undesired vegetation is very damaging to useful crops such as rice. In the current world situation, wherein food shortages are acute, it is most important not to lose a significant portion of a valuable crop such as wheat or rice. The presence of undesired vegetation results in the loss of a significant portion of such crops. Thus, the need exists for a particularly effective herbicide which will destroy as much of this unwanted vegetation as is possible without causing significant damage to the desired crops, e.g. wheat.

According to the instant invention, compounds have been discovered which are highly active herbicides and yet cause minimal damage to certain desired crops, e.g., wheat and rice.

It is understood that all of the compounds disclosed in the instant case are not novel; they are however, all active herbicides.

DESCRIPTION OF THE INVENTION

This invention relates to the compounds of Formula I, all of which are not novel, and to agricultural compositions containing them, and to the method of use of these compounds as selective, as well as general, herbicides having both pre- and post-emergence activity:

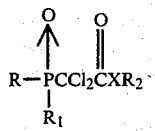
R—PCCl$_2$CXR$_2$
|
R$_1$
I wherein
R is cycloalkoxy of 5–6 carbons, alkoxy of 1–6 carbons, alkoxy of 2–3 carbons substituted with alkoxy of 1–3 carbons, or with 1–3 chlorines or with one bromine, alkenyloxy of 3–4 carbons, phenoxy optionally substituted with chlorine or bromine, methoxy, alkyl group of 1–4 carbons, or nitro group, phenylthio or —NR$_3$R$_4$; wherein R$_3$ is hydrogen, alkyl of 1–4 carbons, cycloalkyl of 5–6 carbons, or

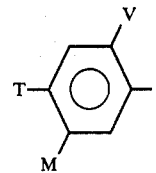

where
V is H, F, Cl, NO$_2$
T is H, F, Cl, Br, C$_1$-C$_3$ alkyl, CF$_3$
M is H, Cl, C$_1$-C$_3$ alkoxy, CF$_3$ provided M and T are not simultaneously CF$_3$;
R$_4$ is hydrogen, or alkyl of 1–4 carbons or methoxy provided that when R$_4$ is methoxy then R$_3$ is hydrogen or methyl;
R$_3$ and R$_4$ may also be taken together to form a bridge having the structure

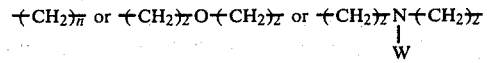

where
n is 4, 5 or 6 and W is hydrogen, methyl or ethyl.
R$_1$ is alkoxy of 1–6 carbons, C$_2$-C$_3$ alkoxy substituted with an alkoxy of 1–3 carbons or with 1–3 chlorines or with one bromine, alkenyloxy of 3–4 carbons, or NR$_3$R$_4$;
wherein
R$_3$ and R$_4$ are as previously defined
R and R$_1$ may be taken together to form a bridge of the structure

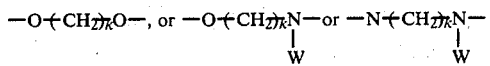

each of which may be optionally substituted with 1–2 alkyls of 1–2 carbons, where k is 2 or 3, and where W is as previously defined;
X is oxygen or sulfur; and
R$_2$ is

—CHR$_7$,
|
R$_8$ alkenyl of 3–4 carbons, or cycloalkyl of 5–6 carbons optionally substituted with methyl
where
R$_7$ is alkyl of 1–3 carbons and
R$_8$ is alkyl of 1–3 carbons.

In the above novel compositions, it must be provided that (1) when R and R$_1$ are both 1-methylpropoxy and X is oxygen or sulfur, R$_2$ must not be 1-methylpropyl, (2) when R and R$_1$ are both methoxy, R$_2$ cannot be allyl, and (3) when R and R$_1$ are both ethoxy, R$_2$ cannot be 1-methylethyl.

Preferred for economical and/or for reasons of higher activity are the following groups of compounds of Formula I;
(1) Those compounds wherein X is oxygen;
(2) Those wherein R$_2$ is

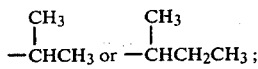

(3) Those wherein
X is oxygen and
$R_2$ is $-CH(CH_3)_2$ or

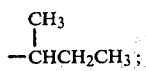

(4) Those of Group 3 wherein
R and $R_1$ are independently alkoxy of 1-4 carbons, alkoxy $C_2$-$C_3$ substituted with alkoxy of 1-3 carbons, $NR_3R_4$ wherein $R_3$ and $R_4$ are as previously defined;

(5) Those compounds of Group 3 wherein
R and $R_1$ are independently alkoxy of 1-4 carbons, alkoxy $C_2$-$C_3$ substituted with alkoxy of 1-3 carbons, or $NR_3R_4$ wherein
$R_3$ and $R_4$ are independently hydrogen or alkyl of 1-4 carbons and
$R_3$ and $R_4$ may also be taken together to form a bridge as previously defined;

(6) Those compounds of Group 5 wherein
R or $R_1$ is alkoxy of 1-4 carbons;

(7) Those compounds of Group 5 wherein
R and $R_1$ are alkoxy of 1-4 carbons.

Specifically preferred for their outstanding activity and/or very favorable cost, or both are:

1-methylpropyl-2,2-dichloro-2-(diethoxyphosphinyl)-acetate 1-methylethyl 2,2-dichloro-2-(diethoxyphosphinyl)-acetate 1-methylethyl-2,2-dichloro-2[di-(1-methylethoxy)-phosphinyl]acetate 1-methylethyl 2,2-dichloro-2-[di-(1-methylpropoxy)-phosphinyl]acetate 1-methylpropyl 2,2-dichloro-2-[di-(1-methylethoxy)-phosphinyl]acetate 1-methylethyl 2,2-dichloro-2-[di-(n-propyloxy)-phosphinyl]acetate 1-methylethyl 2,2-dichloro-2-[diethylamino(ethoxy)-phosphinyl]acetate 1-methylethyl 2,2-dichloro-2-(ethoxy-(ethylamino)-phosphinyl]acetate 1-methylethyl 2,2-dichloro-2-[di-(2-methoxyethoxy)-phosphinyl]acetate 1-methylethyl 2,2-dichloro-2-[(1-morpholinyl)(1-methylethoxy)phosphinyl]acetate This invention also relates to novel compounds of Formula II

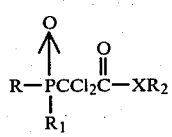

wherein
R is cycloalkoxy of 5-6 carbons, alkoxy of 1-6 carbons, alkoxy of $C_2$-$C_3$ substituted with alkoxy of 1-3 carbons or with 1-3 chlorines or with one bromine, alkenyloxy of 3-4 carbons, phenoxy optionally substituted with chlorine, bromine, methoxy, $C_1$-$C_4$ alkyl, or nitro group, phenylthio, or -$NR_3R_4$ wherein
$R_3$ and $R_4$ are as previously defined for Formula I provided that when $R_4$ is methoxy $R_3$ is hydrogen or methyl.
$R_1$ is as previously defined for Formula I.
X is oxygen or sulfur.
$R_2$ is as defined for Formula I.
provided that
(1) When R and $R_1$ are both 1-methylethoxy and X is oxygen, $R_2$ must not be 1-methylethyl;
(2) When R and $R_1$ are both methoxy or ethoxy and X is oxygen $R_2$ must not be 1-methylethyl;
(3) When R and $R_1$ are both 1-methylpropoxy and X is oxygen or sulfur, $R_2$ must not be 1-methylpropoxy;
(4) When R and $R_1$ are both methoxy, $R_2$ cannot be allyl.
(5) When $R_2$ is 1-methylethyl and one of R or $R_1$ is n-propyloxy then the other of R or $R_1$ cannot be n-butyloxy.

Preferred are the following groups of compounds of Formula II:
(1) Those compounds of Formula II wherein X is oxygen;
(2) Those compounds of groups (1) wherein $R_2$ is

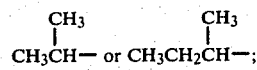

(3) Those compounds of group 2 wherein
R is as previously defined
$R_1$ is $C_2$-$C_3$ alkoxy substituted with alkoxy $C_1$-$C_3$, or $NR_3R_4$; $R_3$ and $R_4$ are as previously defined;
(4) Those compounds of groups 3 wherein
$R_1$ is $C_2$-$C_3$ alkoxy substituted with alkoxy $C_1$-$C_3$;
(5) Those compounds of group (3) wherein $R_1$ is $NR_3R_4$;
(6) Those compounds of group (5) wherein
$R_1$ is $NR_3R_4$ and
$R_3$ is H, alkyl $C_1$-$C_3$,
$R_4$ is H, alkyl $C_1$-$C_3$, methoxy, provided that when $R_4$ is methoxy, $R_3$ is H or methyl.

$R_3$ and $R_4$ may also be taken together to form a bridge having the structure

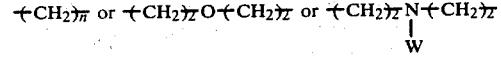

wherein n and W are as previously defined.
(7) Those compounds of groups 5 and 6 wherein R is alkoxy $C_1$-$C_3$ or $C_2$-$C_3$ alkoxy substituted with alkoxy $C_1$-$C_3$.

Specifically preferred are the following compounds of Formula II:

1-methylpropyl-2,2-dichloro-2-(diethoxyphosphinyl)-acetate 1-methylethyl 2,2-dichloro-2[di-(1-methylpropoxy)-phosphinyl]acetate 1-methylpropyl 2,2-dichloro-2-[di-(1-methylethoxy)-phosphinyl]acetate 1-methylethyl 2,2-dichloro-2-[di-(n-propyloxy)-phosphinyl]acetate 1-methylethyl 2,2-dichloro-2-[diethylamino(ethoxy)-phosphinyl]acetate 1-methylethyl 2,2-dichloro-2-(ethoxy-(ethylamino)-phosphinyl]acetate 1-methylethyl 2,2-dichloro-2-[di-(2-methoxyethoxy)-phosphinyl]acetate 1-methylethyl 2,2-dichloro-2-[(1-morpholinyl)(1-methylethoxy)phosphinyl]acetate It is to be understood that all isomers of Formula I resulting from asymmetry at either the phosphorous and/or carbon atoms are included within the scope of this invention.

Methods of Preparation

The compounds of Formula I can be prepared, as shown in Equation A, by chlorination of compounds of Formula II with a metal hypochlorite as described in U.S. Pat. No. 3,624,188 the disclosure of which is herein incorporated by reference. The reaction is carried out in aqueous media at a pH greater than seven, and at a temperature between 0° and 75° C. The compounds of Formulas I and II are not appreciably soluble in the reaction media under these conditions, therefore the reaction mixture consists of two phases.

EQUATION A

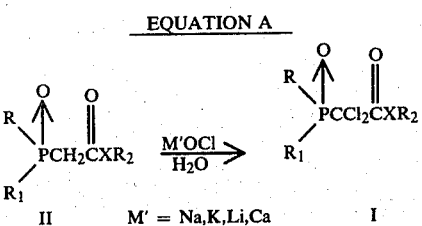

wherein R-R$_2$, and X are as previously defined.

Compounds of Formula I may also be prepared, as shown in Equation B, by chlorination of compounds of Formula II with sulfuryl chloride or with chlorine in the presence of actinic radiation as described in N. D. Bodnarchuk, C. V. Malovik, and G. I. Derkach J. Gen. Chem. (USSR) 39, 1673–1677 (1968) [CA 71, 12452e (1968)]. These reactions may be carried out either without solvent or with the addition of an appropriate inert solvent such as, for example, chloroform, carbon tetrachloride, benzene, or tetrachloroethane.

EQUATION B

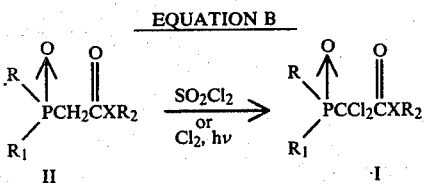

wherein R-R$_2$, and X are as previously defined.

The compounds of Formula II can be prepared, as shown in Equation C, by reaction of a phosphite of Formula III with an α-haloacetate of Formula IV as described in Organophosphorus Compounds—G. M. Kosolapoff, John Wiley and Sons, Inc. New York, 1950, pp. 121–123. The reaction may be carried out at temperatures between 50° and 175° C., and either with or without an added inert organic solvent such as benzene, toluene, or xylene.

EQUATION C

-continued

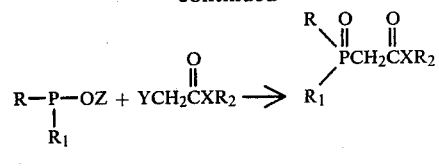

wherein R-R$_2$, and X are as previously defined; Y is chlorine, bromine, or iodine; and Z is an alkyl group of one to six carbons.

Phosphites of Formula III can be prepared by a suitable modification of the methods described in Organophosphorus Compounds—G. M. Kosolapoff, John Wiley and Sons Inc., New York, 1950, pp. 180–210, and D. W. White, R. D. Bartrand, G. K. McEwen, and J. G. Verkade, J. Amer. Chem. Soc. 92, 7125–7135 (1970).

Other compounds of Formula I are more conveniently made by the method described in Equation D.

EQUATION D

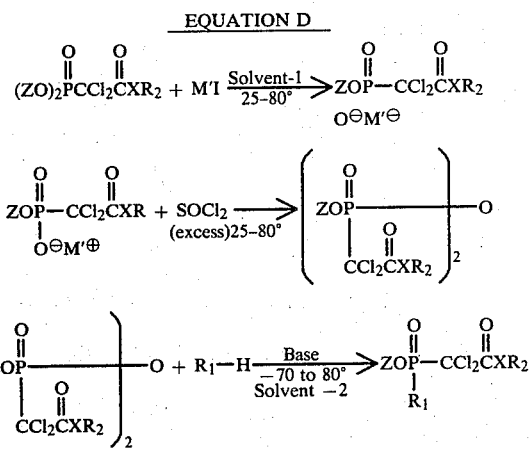

wherein

R$_1$, R$_2$, X, and Z are as previously defined.

M' is sodium, lithium, or potassium.

Solvent -1 is a solvent in which the metal iodide is soluble to the extent of at least 5 weight percent e.g., tetrahydrofuran, methylethyl ketone, or acetone.

Base is trialkylamine, alkali metal alkoxide, or alkali metal hydride.

Solvent -2 is an inert organic solvent such as tetrahydrofuran, diethylether, chloroform, or toluene.

Still other compounds of Formula I may be more conveniently made by the method described in Equation E.

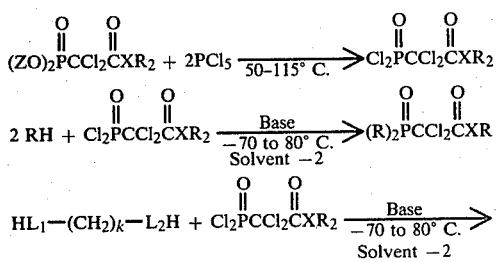

-continued

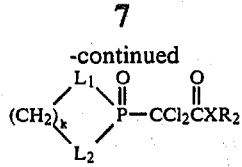

wherein R, R$_2$, K, X, Z, Base, and Solvent -2 are as previously defined, and $-(CH_2)_k$ may be optionally substituted with 1-2 alkyls of 1-2 2 carbons; and L$_1$, L$_2$ are independently oxygen or -N-W, wherein W is as previously defined.

The following examples specifically illustrate this invention. Unless otherwise indicated, all parts are by weight and all temperatures in °C. Proton NMR data was taken at 60 MHZ.

EXAMPLE 1

To 19.5 g of 1-methylpropyl bromoacetate heated to 50°, was added 18.2 g of triethyl phosphite over a ½ hour period. The temperature rose to 140°. The temperature was kept at 140° for an additional 15 minutes. Volatile products were removed by maintaining the reaction mixture at 65° C. under 1 mm pressure for 30 minutes. The yield of 1-methylpropyl 2-(diethoxyphosphinyl)acetate was 25.8 g as a pale yellow oil N$_D^{27}$=1.4278. IR(Neat)$\nu$MAX=1730 cm$^{-1}$ (C=O). NMR (CDCl$_3$) $\delta$ 0.8-1.8 (complex multiplet, 14H); 3.1 (d J$_{PCH}$=22 Hz, 2H); 4.3 (m, 4H); 5.1 (m, 1H).

Using suitable modifications of the above procedure, the intermediates of Formula III can be prepared.

EXAMPLE 2

A mixture of 185 ml of 5.25% commercial grade sodium hypochlorite solution (Clorox ®) and 100 ml of carbon tetrachloride was cooled to 0° C. To this mixture, with vigorous stirring, was added a solution of 12.6 g of 1-methylpropyl 2-(diethoxyphosphinyl)-acetate in 50 ml of carbon tetrachloride over a ½ hour period. During this addition the temperature was kept at 0°-5° and the pH at 9.0-9.5 by the simultaneous addition of 1 N hydrochloric acid. The reaction mixture was stirred an additional 15 minutes at 0°-5° C. The carbon tetrachloride layer was washed with water, dried over magnesium sulfate and stripped at 60° C./1 mm pressure to yield 16.0 g of 1-methylpropyl 2,2-dichloro-2-(diethoxyphosphinyl)acetate as a pale yellow oil N$_D^{27}$=1.4524.

IR (Neat) $\nu$MAX=1740 cm$^{-1}$ (C=O). NMR (CDCl) $\delta$ 0.9-2.1 (complex multiplet, 14H); 4.3-4.8 (m, 4H); 4.9-5.4 (m, 1H); distillation of this oil in a Kugelrohr apparatus at approximately 100° C. and at 0.1 mm Hg gave a pale yellow oil N$_D^{27}$=1.4523.

EXAMPLE 3

A solution of 160.5 g of 1-methylpropyl 2,2-dichloro-2-(diethoxyphosphinyl)acetate and 75 g of sodium iodide in 800 ml of methylethyl ketone was stirred at 25° for 20 hours. The precipitate was filtered off, washed with methylethyl ketone and dried to give 91.8 g of 1-methylpropyl 2,2-dichloro-2-(ethoxyhydroxyphosphinyl)acetate sodium salt, m.p. 245°-8°.

NMR(DMSO-d$_6$) $\delta$ 0.8-1.9 (m, 11.3H); 3.9-4.4 (m, 1.8H); 4.8-5.2 (m, 0.9H).

EXAMPLE 4

A mixture of 31.5 g of powdered 1-methylpropyl 2,2-dichloro-2-(ethoxyhydroxyphosphinyl)acetate sodium salt and 100 ml of thionyl chloride was stirred at reflux temperature (79°) for two hours. The mixture was cooled to room temperature and 100 ml of n-butylchloride was added to it. This mixture was filtered through Celite ® and the filtrate stripped in vacuum to give 23.4 g of di(1-methylpropyl)bis(2,2-dichloro)-2,2'-[oxybis(ethoxyphosphinyl)]acetate as a viscous orange oil.

NMR(CDCl$_3$) $\delta$ 0.8-2.0 (m, 22.2H); 4.5-4.9 (m, 4.0H); 5.0-5.5(m, 1.8H)

Mass Spectrum: M/e=567 (M⊕1); 511[567-56 (CH$_3$CH=CHCH$_3$)]; 455 [511-56(CH$_3$CH=CHCH$_3$)].

EXAMPLE 5

To a solution of 9.3 g of di(1-methylpropyl)bis (2,2-dichloro)-2,2'-[oxybis(ethoxyphosphinyl)]acetate in 100 ml of diethylether was added 5 ml of dimethylamine. The reaction mixture was stirred at 20° for 1 hour and at reflux for 1 hour. The reaction mixture was cooled and filtered, and the filtrate washed with water, dried and stripped in vacuum to give a clear oil. Kugelrohr distillation of this oil at 80°-130° and 1 mm pressure gave 1.5 g of 1-methylpropyl 2,2-dichloro-2-[ethoxy(dimethylamino)phosphinyl]acetate as a clear oil.

NMR(CDCl$_3$) $\delta$ 1.0-1.4 (m, 11H); 3.0(d, J=8 Hz, 6H); 1.45 (qt, 2H); 5.2 (m, 1H).

EXAMPLE 6

To 9.05 g isopropyl bromoacetate was added 11.05 g of diethyl N,N-di(1-methylethyl)phosphoramidite dropwise under a nitrogen atmosphere at 120°. The reaction was completed by slowly warming to 150°. The resulting 1-methylpropyl 2-[ethoxy di(1-methylethyl)aminophosphinyl]acetate, 12.0 g was used without further purification.

NMR(CDCl$_3$) $\delta$ 1.3 (d, J=7 Hz, 21H); 2.8 (d, J=20 Hz, 2H); 3.2-4.4 (m, 4H); 5.0 (qt, 1H).

EXAMPLE 7

To 100 ml of 5.25 percent sodium hypochlorite solution (Clorox ®) was added 6.0 g of 1-methylpropyl 2-[ethoxy di(1-methylethyl)aminophosphinyl]acetate dropwise. The pH was maintained at 10.5-11.0 by simultaneous addition of 1 N HCl solution. The reaction mixture was stirred an additional 45 minutes then extracted with methylene chloride. The methylene chloride solution was dried and stripped in vacuum to give 6.2 g of 1-methylethyl 2,2-dichloro-2-[ethoxy di(1-methylethyl)aminophosphinyl]acetate as an acid.

NMR(CDCl$_3$) $\delta$ 1.4 (m, 21H); 3.6 (m, 2H); 4.2 (m, 2H); 5.1 (qt, 1H).

Mass Spectrum: M/e=346[M-15(CH$_3$)], 319[M-42 (CH$_3$CH=CH$_2$], 262(M-99(Me$_2$CHN=CMe$_2$)].

EXAMPLE 8

A mixture of 200 g of 1-methylpropyl 2,2-dichloro-2-(diethoxyphosphinyl)acetate and 333 g of powdered phosphorus pentachloride was stirred at 100°-108° for 32 hours. The byproduct phosphorus oxychloride was removed by stripping under vacuum and the residue subjected to Kugelrohr distillation at 0.2 mm to give 130 g boiling 50°-100°. This material was distilled through a 200 mm Vigreux column to give 43 g of 1-methylpropyl 2,2-dichloro-2-(dichlorophosphinyl)acetate as an oil bp 79°-86°/0.2 mm.

NMR (CDCl$_3$) $\delta$0.8-2.0 (m, 8.0H); 5.0-5.6 (m, 1.0H).
IR (Neat) 1770 cm$^{-1}$ (doublet), >c=o; 1240 1300 cm$^{-1}$, >P=O.

EXAMPLE 9

A solution of 5.3 g of N,N'-dimethylethylenediamine and 12.6 g of triethylamine in 100 ml of diethylether was added to a solution of 18.1 g of 1-methylpropyl 2,2-dichloro-2-(dichlorophosphinyl)-acetate in 250 ml of diethylether at 15°–20° over a 45 minute period. After stirring an additional 1 hour at room temperature, the reaction mixture was washed with water, 5% sodium bicarbonate solution and dried and stripped under vacuum. The residue was subjected to Kugelrohr distillation to give 7.0g of 1-methylpropyl $\alpha,\alpha$-dichloro-1,3-dimethyl-2-oxo-1,3,2-diazophospholidine-2-acetate bp 130°–155°/0.25 mm.

NMR (CDCl$_3$) $\delta$0.8-2.0 (m, 8H);, 2.75 and 2.90 (d, 5.8H); 3.2-3.5 (m, 4.3H); 4.8-5.3 (m, 0.9H).

Mass Spectrum: M/e=316 (M⊕); 260[M-56(C$_4$H$_8$); 216[260-44(CO$_2$)].

Using suitable modifications of the procedures described in the proceeding examples, the compounds of Formula I described in Table 1 can be prepared.

TABLE I $$\begin{array}{c} R \\ \phantom{R}\diagdown \phantom{O} \\ \phantom{RRR}P-CCl_2CXR_2 \\ \phantom{R}\diagup \\ R_1 \end{array} \quad \begin{array}{c} O \phantom{xx} O \\ \| \phantom{xx} \| \end{array}$$

| R | R$_1$ | X | R$_2$ | N$_D^{27}$ | bp(mp) | $\nu_{C=O}$ ($\mu$) |
|---|---|---|---|---|---|---|
| C$_2$H$_5$O— | C$_2$H$_5$O— | O | (CH$_3$)$_2$CH | 1.4508 | | |
| (CH$_3$)$_2$CHO— | (CH$_3$)$_2$CHO— | O | (CH$_3$)$_2$CH | 1.4430 | | |
| C$_2$H$_5$O— | C$_2$H$_5$O— | O | (thiacyclohexyl–S–) | 1.4715 | | |
| C$_2$H$_5$CHO—<br>\|<br>CH$_3$ | C$_2$H$_5$CHO—<br>\|<br>CH$_3$ | O | (CH$_3$)$_2$CH— | 1.4501 | | |
| (CH$_3$)$_2$CHO— | (CH$_3$)$_2$CHO— | O | C$_2$H$_5$CH—<br>\|<br>CH$_3$ | 1.4481 | | |
| C$_2$H$_5$CHO—<br>\|<br>CH$_3$ | C$_2$H$_5$CHO—<br>\|<br>CH$_3$ | O | C$_2$H$_5$CH—<br>\|<br>CH$_3$ | 1.4475 | | |
| (CH$_3$)$_2$CH—O | (CH$_3$)$_2$CHO— | O | [(CH$_3$)$_2$CH]$_2$CH— | 1.4492 | | |
| C$_2$H$_5$O— | C$_2$H$_5$O— | O | [(CH$_3$)$_2$CH]$_2$CH— | 1.4561 | | |
| C$_2$H$_5$O— | C$_2$H$_5$O— | O | CH$_3$CH$_2$CH$_2$CH—<br>\|<br>CH$_3$ | 1.4504 | | |
| C$_2$H$_5$O— | C$_2$H$_5$O— | O | (CH$_3$CH$_2$)$_2$CH— | 1.4534 | | |
| C$_2$H$_5$O— | C$_2$H$_5$O— | O | (CH$_3$)$_2$CH—CH—<br>\|<br>CH$_3$ | 1.4529 | | |
| C$_2$H$_5$O— | C$_2$H$_5$O— | O | (2-methylthiacyclohexyl, CH$_3$ on S-ring) | 1.4745(18°) | | |
| CH$_3$O— | CH$_3$O— | O | (CH$_3$)$_2$CH— | 1.4574 | | |
| CH$_3$O— | CH$_3$O— | O | C$_2$H$_5$CH—<br>\|<br>CH$_3$ | 1.4616(20°) | | |
| CH$_2$=CHCH$_2$O— | CH$_2$=CHCH$_2$O— | O | (CH$_3$)$_2$CH— | 1.4699 | | |
| CH$_2$=CHCH$_2$O— | CH$_2$=CHCH$_2$O— | O | C$_2$H$_5$CH—<br>\|<br>CH$_3$ | 1.4693 | | |
| CH$_3$CH$_2$CH$_2$O— | CH$_3$CH$_2$CH$_2$O— | O | (CH$_3$)$_2$CH— | 1.4511 | | |
| CH$_3$CH$_2$CH$_2$O— | CH$_3$CH$_2$CH$_2$O— | O | C$_2$H$_5$CH—<br>\|<br>CH$_3$ | 1.4550(20°) | | |
| n-C$_4$H$_9$O— | n-C$_4$H$_9$O— | O | (CH$_3$)$_2$CH— | 1.4497 | | |
| n-C$_4$H$_9$O— | n-C$_4$H$_9$O— | O | C$_2$H$_5$CH—<br>\|<br>CH$_3$ | 1.4504 | | |
| CH$_2$=C—CH$_2$O—<br>\|<br>CH$_3$ | CH$_2$=CH—CH$_2$O—<br>\|<br>CH$_3$ | O | (CH$_3$)$_2$CH— | 1.4733 | | |
| ClCH$_2$CH$_2$O— | ClCH$_2$CH$_2$O— | O | (CH$_3$)$_2$CH— | 1.4818 | | |
| ClCH$_2$CH$_2$O— | ClCH$_2$CH$_2$O— | O | C$_2$H$_5$CH—<br>\|<br>CH$_3$ | 1.4810 | | |
| (CH$_3$)$_2$CHO— | (CH$_3$)$_2$CHO— | O | CH$_2$=C—CH$_2$O—<br>\|<br>CH$_3$ | 1.4628 | | |
| (CH$_3$)$_2$CHO— | (CH$_3$)$_2$CHO— | O | CH$_2$=CHCH$_2$O— | | | |

TABLE I-continued $$\underset{R_1}{\overset{R}{\phantom{x}}}\overset{O}{\underset{\phantom{x}}{P}}-CCl_2\overset{O}{\underset{\phantom{x}}{C}}XR_2$$

| R | R₁ | X | R₂ | $N_D^{27}$ | bp(mp) | $\nu_{C=O}$ ($\mu$) |
|---|---|---|---|---|---|---|
| CH₃O— | CH₃O— | O | CH₃CH₂CH₂CH— <br>             \|<br>            C₂H₅ | 1.4586 | | |
| CH₃O— | CH₃O— | O | 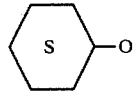 | 1.4770 | | |
| C₂H₅O— | C₂H₅O— | O | 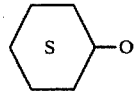 | 1.4732 | | |
| (CH₃)₂CH—CH₂O— | (CH₃)₂CHCH₂O— | O | (CH₃)₂CH— | 1.4509 | | |
| (CH₃)₂CHCH₂O— | (CH₃)₂CHCH₂O— | O | C₂H₅CH—<br>      \|<br>      CH₃ | 1.4501 | | |
| CH₃OCH₂CH₂O— | CH₃OCH₂CH₂O— | O | (CH₃)₂CH— | 1.4650 | | |
| CH₃OCH₂CH₂O— | CH₃OCH₂CH₂O— | O | C₂H₅CH—<br>      \|<br>      CH₃ | 1.4582 | | |
| C₂H₅O— | C₂H₅O— | O | CH₂=CHCH—<br>          \|<br>          CH₃ | 1.4481 | | |
| CH₃CH₂CH₂CH₂CHO—<br>                \|<br>                CH₃ | CH₃CH₂CH₂CH₂CHO—<br>                \|<br>                CH₃ | O | (CH₃)₂CH— | | | |
| C₂H₅CHO—<br>   \|<br>   CH₃ | C₂H₅O— | O | (CH₃)₂CH— | 1.4491 | | |
| C₂H₅CHO—<br>   \|<br>   CH₃ | CH₃O— | O | (CH₃)₂CH— | 1.4529 | | |
| C₂H₅CHO—<br>   \|<br>   CH₃ | CH₃O— | O | C₂H₅CH—<br>      \|<br>      CH₃ | 1.4535 | | |
| 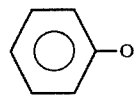 | CH₃O— | O | (CH₃)₂CH— | 1.4712 | 120°–30°/<br>0.25mm | |
| 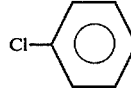 | CH₃O— | O | C₂H₅CH—<br>      \|<br>      CH₃ | | 140°–60°/<br>0.25mm | |
| C₂H₅O—CH₂CH₂CH₂O— | C₂H₅OCH₂CH₂CH₂O— | O | (CH₃)₂CH— | | | |
| CH₃OCH₂CH₂CH₂O— | CH₃OCH₂CH₂CH₂O— | O | (CH₃)₂CH— | | | |
| 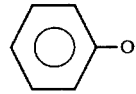 | C₂H₅O— | O | (CH₃)₂CH— | 1.5003 | 170°/<br>0.1mm | |
| Cl—⬡—O— | C₂H₅O— | O | (CH₃)₂CH— | 1.5058 | | |
| ⬡—O— | (CH₃)₂CHO— | O | (CH₃)₂CH— | 1.4914 | | |

TABLE I-continued $$\overset{R}{\underset{R_1}{\diagdown}}\overset{O}{\overset{\|}{P}}-CCl_2\overset{O}{\overset{\|}{C}}XR_2$$

| R | $R_1$ | X | $R_2$ | $N_D^{27}$ | bp(mp) | $\nu_{C=O}$ ($\mu$) |
|---|---|---|---|---|---|---|
| 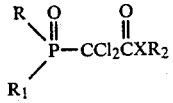 3-methylphenoxy | $C_2H_5O-$ | O | $(CH_3)_2CH-$ | 1.4963 | | |
|  3-methylphenoxy | $C_2H_5O-$ | O | $C_2H_5CH(CH_3)-$ | 1.4946 | | |
| 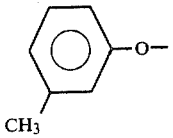 2-chlorophenoxy | $C_2H_5O-$ | O | $(CH_3)_2CH-$ | 1.5059 | | |
| 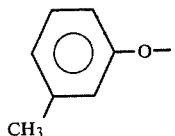 2-chlorophenoxy | $C_2H_5O-$ | O | $C_2H_5CH(CH_3)-$ | 1.5049 | | |
| 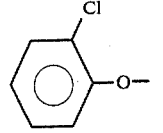 4-methoxyphenoxy | $C_2H_5O-$ | O | $(CH_3)_2CH-$ | 1.5013 | | |
| 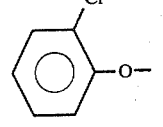 4-methoxyphenoxy | $C_2H_5O-$ | O | $C_2H_5CH(CH_3)-$ | 1.4998 | | |
| 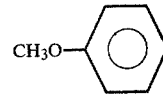 2-isopropyl-4-chlorophenoxy | $C_2H_5O-$ | O | $(CH_3)_2CH-$ | | | |
| 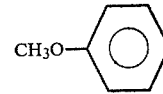 2-nitro-4-chlorophenoxy | $C_2H_5O-$ | O | $C_2H_5CH(CH_3)-$ | | | |
| 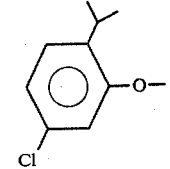 phenylthio | $C_2H_5O-$ | O | $(CH_3)_2CH-$ | 1.5392 | | |
| 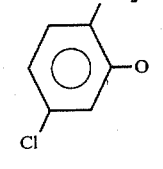 phenylthio | $C_2H_5O-$ | O | $C_2H_5CH(CH_3)-$ | 1.5314 | | |
| 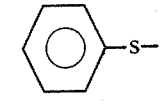 2-nitro-4-methylphenoxy | $(CH_3)_2CHO-$ | O | $(CH_3)_2CH-$ | | | |

TABLE I-continued $$\underset{R_1}{\overset{R'}{\phantom{|}}}\overset{O}{\underset{\|}{P}}-CCl_2CXR_2$$

| R | $R_1$ | X | $R_2$ | $N_D^{27}$ | bp(mp) | $\nu_{C=O}$ (μ) |
|---|---|---|---|---|---|---|
| 4-O₂N-C₆H₄-O— | (CH₃)₂CHO— | O | (CH₃)₂CH— | | | |
| 3-O₂N-C₆H₄-O— | (CH₃)₂CHO— | O | (CH₃)₂CH— | | | |
| 2-O₂N-C₆H₄-O— | (CH₃)₂CHO— | O | (CH₃)₂CH— | | | |
| 2-isopropyl-C₆H₄-O— | (CH₃)₂CHO— | O | (CH₃)₂CH— | | | |
| 4-isopropyl-C₆H₄-O— | (CH₃)₂CHO— | O | (CH₃)₂CH— | | | |
| 3-Br-C₆H₄-O— | (CH₃)₂CH— | O | (CH₃)₂CH— | | | |
| 2-Cl-4-CH₃-C₆H₃-O— | C₂H₅O— | O | (CH₃)₂CH— | | | |
| 3-Cl-C₆H₄-O— | C₂H₅O— | O | (CH₃)₂CH— | | | |
| 4-CH₃O-2-NO₂-C₆H₃-O— | C₂H₅O— | O | (CH₃)₂CH— | | | |
| BrCH₂CH₂O— | BrCH₂CH₂O— | O | (CH₃)₂CH— | | | |
| CCl₃CH₃O— | CCl₃CH₂O— | O | (CH₃)₂CH— | | | |
| —OCH(CH₃)—CH₂O—CH(CH₃)— | | O | C₂H₅CH(CH₃)— | 1.4733 | | |
| 2,4,5-Cl₃-C₆H₂-NH— | (CH₃)₂CHO | O | (CH₃)₂CH— | | | |

TABLE I-continued $$\underset{R_1}{\overset{R}{\diagdown}}\overset{O}{\underset{\|}{P}}-\overset{O}{\underset{\|}{C}}Cl_2CXR_2$$

| R | $R_1$ | X | $R_2$ | $N_D^{27}$ | bp(mp) | $\overset{\nu}{\diagup}C=O$ ($\mu$) |
|---|---|---|---|---|---|---|
| 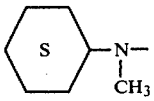 | $C_2H_5O$ | O | $(CH_3)_2CH-$ | | | |
| $CH_3ONH-$ | $CH_3ONH-$ | O | $(CH_3)_2CH-$ | | | |
| $CH_3ONH-$ | $(CH_3)_2CHO-$ | O | $(CH_3)_2CH-$ | | | |
| $\underset{\overset{|}{CH_3}}{CH_3ON-}$ | $\underset{\overset{|}{CH_3}}{CH_3ON-}$ | O | $(CH_3)_2CH-$ | | | |
| $\underset{\overset{|}{CH_3}}{CH_3ON-}$ | $(CH_3)_2CHO-$ | O | $(CH_3)_2CH-$ | | | |
| 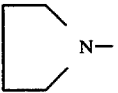 | $C_2H_5O-$ | O | $(CH_3)_2CH-$ | | | |
| 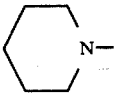 | $C_2H_5O-$ | O | $(CH_3)_2CH-$ | 1.4770(25°) | | |
| 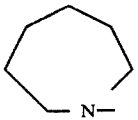 | $C_2H_5O-$ | O | $(CH_3)_2CH-$ | | | |
| 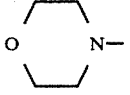 | $C_2H_5O-$ | O | $(CH_3)_2CH-$ | 1.4927(25°) | | |
| 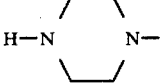 | $C_2H_5O-$ | O | $(CH_3)_2CH-$ | | | |
|  | $C_2H_5O$ | O | $(CH_3)_2CH-$ | | | |
| $H_2N-$ | $(CH_3)_2CHO-$ | O | $(CH_3)_2CH-$ | | | |
| 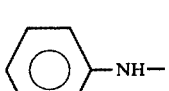 | $C_2H_5O$ | O | $(CH_3)_2CH-$ | 1.4930(25°) | | |
| 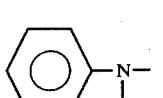 | $C_2H_5O-$ | O | $(CH_3)_2CH-$ | | | |
| 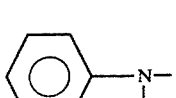 | $C_2H_5O-$ | O | $(CH_3)_2CH$ | | | |

TABLE I-continued $$\underset{R_1}{\overset{R}{\diagdown}}\overset{O}{\underset{\|}{P}}-\overset{O}{\underset{\|}{CCl_2CXR_2}}$$

| R | $R_1$ | X | $R_2$ | $N_D^{27}$ | bp(mp) | $\nu_{C=O}$ (μ) |
|---|---|---|---|---|---|---|
| 4-Cl-C₆H₄-NH— | $C_2H_5O$— | O | $(CH_3)_2CH$— | | | |
| 4-Cl-2-F-C₆H₃-NH— | $C_2H_5O$— | O | $(CH_3)_2CH$— | | | |
| 3-Br-C₆H₄-NH— | $C_2H_5O$— | O | $(CH_3)_2CH$— | | | |
| 2-Cl-C₆H₄-NH— | $C_2H_5O$— | O | $(CH_3)_2CH$— | | | |
| 3,4-Cl₂-C₆H₃-NH— | $C_2H_5O$— | O | $(CH_3)_2CH$— | | | |
| 2-NO₂-C₆H₄-NH— | $C_2H_5O$— | O | $(CH_3)_2CH$— | | | |
| 4-CH₃-C₆H₄-NH— | $C_2H_5O$— | O | $(CH_3)_2CH$— | | | |
| 4-iPr-C₆H₄-NH— | $C_2H_5O$— | O | $(CH_3)_2CH$— | | | |
| (CH₃)₂CH—O(CH₂)₃—O— | (CH₃)₂CH—O(CH₂)₃O— | O | $CH_3CH_2CH(CH_3)$— | | | |
| (CH₃)₂CH—O—CH(CH₃)—CH₂—O— | (CH₃)₂CH—OCH(CH₃)CH₂O— | O | $CH_3CH_2CH(CH_3)$— | | | |
| 4-Cl-2-NO₂-C₆H₃-NH— | $C_2H_5O$— | O | $(CH_3)_2CH$— | | | |
| 4-CH₃-3-Cl-C₆H₃-NH— | $C_2H_5O$— | O | $(CH_3)_2CH$— | | | |
| 2,4-Cl₂-6-... wait 2,4-Cl₂,... | $C_2H_5O$— | O | $(CH_3)_2CH$ | | | |

TABLE I-continued $$\underset{R_1}{\overset{R}{\searrow}}\overset{O}{\underset{\|}{P}}-CCl_2C\overset{O}{\underset{\|}{X}}R_2$$

| R | R₁ | X | R₂ | $N_D^{27}$ | bp(mp) | $\nu_{C=O}$ (μ) |
|---|---|---|---|---|---|---|
| 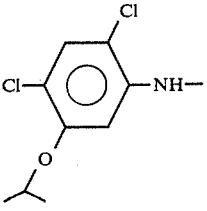 | C₂H₅O— | O | (CH₃)₂CH— | | | |
| 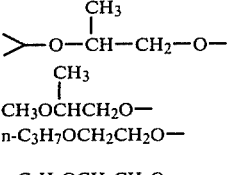 | 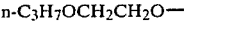 | O | (CH₃)₂CH— | | | |
| CH₃OCHCH₂O—<br>\|<br>CH₃ | CH₃OCHCH₂O—<br>\|<br>CH₃ | O | (CH₃)₂CH— | | | |
| n-C₃H₇OCH₂CH₂O— | | O | (CH₃)₂CH— | | | |
| n-C₃H₇OCH₂CH₂O— | n-C₃H₇OCH₂CH₂O— | O | CH₃CH₂CH—<br>\|<br>CH₃ | | | |
| CCl₃CHO—<br>\|<br>CH₃ | n-C₃H₇OCH₂CH₂O—<br>CCl₃CH—O<br>\|<br>CH₃ | O | CH₃CH₂CH—<br>\|<br>CH₃ | | | |
| ClCH₂CH₂CH₂O— | ClCH₂CH₂CH₂O— | O | CH₃CH₂CH—<br>\|<br>CH₃ | | | |
| BrCH₂CH₂CH₂O— | BrCH₂CH₂CH₂O— | O | CH₃CH₂CH—<br>\|<br>CH₃ | | | |
|  |  | O | (CH₃)₂CH— | | | |
|  | (CH₃)₂N— | O | (CH₃)₂CH— | | | |
| 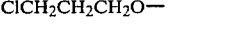 | CH₃ONH— | O | (CH₃)₂CH— | | | |
| 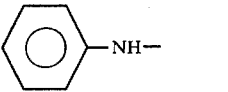 | CCl₃CH₂O— | O | (CH₃)₂CH— | | | |
| (CH₃)₂CHO— | (CH₃)₂CHO | S | C₂H₅CH—<br>\|<br>CH₃ | 1.4828(25) | 150°–5°/<br>2 mm | |
| C₂H₅O— | C₂H₅O— | S | (CH₃)₂CH— | 1.4888(25) | 126°–134°/<br>2 mm | |
| (CH₃)₂CHO— | (CH₃)₂CHO | S | (CH₃)₂CH— | 1.4785(25) | 130°–40°/<br>2 mm | |
| C₂H₅O— | C₂H₅O— | S | C₂H₅CH—<br>\|<br>CH₃ | 1.4890(25) | 130°–40°/<br>2 mm | |
| C₂H₅CHO—<br>\|<br>CH₃ | C₂H₅CHO—<br>\|<br>CH₃ | S | C₂H₅CH—<br>\|<br>CH₃ | 1.4804(25) | | |
| C₂H₅CHO—<br>\|<br>CH₃ | C₂H₅CHO—<br>\|<br>CH₃ | S | (CH₃)₂CH— | 1.4802(25) | | |
| C₂H₅O— | C₂H₅O | S | 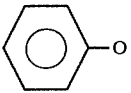 | 1.5103(25) | | |

TABLE I-continued $$\underset{R_1}{\overset{R}{\phantom{|}}}\overset{O}{\underset{\phantom{|}}{P}}-CCl_2\overset{O}{C}XR_2$$

| R | $R_1$ | X | $R_2$ | $N_D^{27}$ | bp(mp) | $\nu_{C=O}$ (μ) |
|---|---|---|---|---|---|---|
| $(CH_3)_2CHO-$ | $(CH_3)_2CHO-$ | S | cyclohexyl | 1.4990(25) | | |
| $ClCH_2\overset{CH_3}{\underset{|}{C}}HO-$ | $ClCH_2\overset{CH_3}{\underset{|}{C}}HO-$ | O | $CH_3CH_2\overset{CH_3}{\underset{|}{C}}H-$ | | | |
| $(C_2H_5)_2N-$ | $C_2H_5O-$ | S | $(CH_3)_2CH-$ | | | 5.68 |
| phenyl-O- | $C_2H_5O-$ | S | $(CH_3)_2CH-$ | | | |
| phenyl-NH- | $C_2H_5O-$ | S | $(CH_3)_2CH-$ | | | |
| $-OCHCH_2CHO-$ with $CH_3$, $CH_3$ | | S | $(CH_3)_2CH-$ | | | |
| $-OCH-CH_2N-$ with $CH_3$, $CH_3$ | | O | $CH_2=CHCH-$ with $CH_3$ | | | |
| $(CH_3)_2CHO-$ | $(CH_3)_2CHO-$ | S | $CH_2=\underset{CH_3}{\underset{|}{C}}-CH-$ | | | |
| piperidinyl-N- | 2-nitro-4-methyl-phenyl-O- | O | $(CH_3)_2CH$ | | | |
| piperidinyl-N- | phenyl-O- | O | $(CH_3)_2CH-$ | | | |
| 4-Cl-phenyl-NH- | 2-nitro-4-methyl-phenyl-O- | O | $(CH_3)_2CH-$ | | | |
| phenyl-O- | $(CH_3)_2N-$ | O | $(CH_3)_2CH-$ | | | |
| 2-tetrahydrothiopyranyl-O- | $(C_2H_5)N-$ | O | $(CH_3)_2CH-$ | | | |
| 3-CF$_3$-phenyl-NH- | $C_2H_5O-$ | O | $(CH_3)_2CH-$ | | | |
| $(ClCH_2)_2CHO$ | $(ClCH_2)_2CHO-$ | O | $CH_3CH_2\overset{CH_3}{\underset{|}{C}}H-$ | | | |

TABLE I-continued
$$\begin{array}{c} R \quad O \quad O \\ \diagdown \parallel \quad \parallel \\ P-CCl_2CXR_2 \\ \diagup \\ R_1 \end{array}$$
| R | R₁ | X | R₂ | $N_D^{27}$ | bp(mp) | $\nu_{C=O}$ (μ) |
|---|---|---|---|---|---|---|
|  | C₂H₅O— | O | (CH₃)₂CH— | | | |
| >—OCH₂CH₂CH₂O | | O | (CH₃)₂CH— | | | |
| | >—OCH₂CH₂CH₂O— | | | | | |
|  | (CH₃)₂CHO | O | (CH₃)₂CH— | | | |
|  | (CH₃)₂CHO— | O | (CH₃)₂CH— | | | |
|  | (CH₃)₂CHO— | O | (CH₃)₂CH— | | | |
|  | (CH₃)₂CHO | O | (CH₃)₂CH— | | | |
|  | (CH₃)₂CHO | O | (CH₃)₂CH— | | | |
|  | (CH₃)₂CHO | O | (CH₃)₂CH— | | | |
|  | (CH₃)₂CHO | O | (CH₃)₂CH— | | | |
|  | (CH₃)₂CHO | O | (CH₃)₂CH— | | | |
|  | (CH₃)₂CHO | O | (CH₃)₂CH— | | | |

TABLE I-continued $$\underset{R_1}{\overset{R}{\diagdown}}\overset{O}{\underset{\|}{P}}-CCl_2\overset{O}{\underset{\|}{C}}XR_2$$

| R | R₁ | X | R₂ | $N_D^{27}$ | bp(mp) | $\nu_{C=O}$ (μ) |
|---|---|---|---|---|---|---|
| 4-F, 3-Cl-C₆H₃-NH— | (CH₃)₂CHO | O | (CH₃)₂CH— | | | |
| 2-Cl, 5-CF₃-C₆H₃-NH— | (CH₃)₂CHO | O | (CH₃)₂CH— | | | |
| (CH₃)₂N— | (CH₃)₂N— | O | (CH₃)₂CH— | | | |
| (C₂H₅)₂N— | (C₂H₅)₂N— | O | (CH₃)₂CH— | | | |
| (CH₃)₂N— | 3-CF₃-C₆H₄-NH— | O | (CH₃)₂CH— | | | |
| (CH₃)₂N— | 2,4-Cl₂-C₆H₃-NH— | O | (CH₃)₂CH— | | | |
| morpholino | morpholino | O | (CH₃)₂CH— | | | |
| morpholino | morpholino | O | CH₃CH₂CH(CH₃)— | | | |
| piperidino | piperidino | O | CH₃CH₂CH(CH₃)— | | | |
| pyrrolidino | pyrrolidino | O | CH₃CH₂CH(CH₃)— | | | |
| hexamethyleneimino | hexamethyleneimino | O | CH₃CH₂CH(CH₃)— | | | |
| CH₃O | CH₃O | O | C₃H₇—CH(C₂H₅)— | 1.4586 | | |
| CH₃O | CH₃O | O | 2-methylcyclopentyl | 1.4732 | | |
| C₂H₅O | NH₂ | O | C₂H₅CH(CH₃)— | 1.4890 | | |
| C₆H₅-O— | (C₂H₅)₂N— | O | (CH₃)₂CH— | 1.5171 | | |

Useful formulations of the compounds of Formula I can be prepared in conventional ways. They include dusts, granules, pellets, solutions, emulsions, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate porportions:

|  | Active Ingredient | Percent by Weight Diluent(s) | Surfactant(s) |
|---|---|---|---|
| Emulsions, Solutions (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. End., Dorland Books, Caldwell, N.J. The denser diluents are preferred for dusts. Typical liquid diluents and solvents are described in Marsden, "Solvents Guide", 2nd Edn., Interscience, New York, 1950. Solution concentrates are preferably stable against phase separation at 0° C. "McCutcheon's Detergents and Emulsifiers Annual", Allured Publ. Corp., Ridgwood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43 through Col. 7, Line 62 and Ex. 8, 12, 15, 39, 41, 52, 53, 58, 132, 138–140, 162–164, 166, 167, 169–182.

H. Gysin and E. Knüsli, U.S. Pat. No. 2,891,855, June 23, 1959, Col. 3, Line 66 through Col. 5, Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 10

Emulsifiable Concentrate

| | |
|---|---|
| 1-methylpropyl 2,2-dichloro-2-(diethoxyphosphinyl)acetate | 25% |
| blend of oil soluble sulfonates and polyoxyethylene ethers | 6% |
| cumene range aromatic solvent | 69% |

The ingredients are combined and stirred with gentle warming to speed solution. A fine screen filter is included in packaging operation to insure the absence of any extraneous undissolved material in the product.

EXAMPLE 11

Pellets—Granules

| | |
|---|---|
| 1-methylpropyl 2,2-dichloro-2-[di-(1-methylethoxy)phosphinyl]acetate | 15% |
| anhydrous sodium sulfate | 10% |
| crude calcium ligninsulfonate | 5% |
| sodium alkylnaphthalenesulfonate | 1% |
| calcium/magnesium bentonite | 69% |

The ingredients are blended and moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

Emulsifiable Concentrate

| | |
|---|---|
| 1-methylethyl 2,2-dichloro-2-[diethylamino(ethoxy)phosphinyl]acetate | 36% |
| blend of oil soluble sulfonates and polyoxyethylene ethers | 8% |
| 2-butoxyethanol | 56% |

The ingredients are combined and stirred until solution is effected. After filtration, the liquid may be used directly in LV or ULV applications or may be emulsified in water before spraying.

EXAMPLE 13

Granules

| | |
|---|---|
| 1-methylethyl 2,2-dichloro-2-[di-(2-methoxyethoxy)phosphinyl]acetate | 5% |
| preformed bentonite granules, 20–50 mesh | 95% |

The active ingredient is dissolved in isopropanol to make a 20% solution which is then sprayed on the preformed granules as they are tumbled in a double cone blender. After drying to remove solvent, the granules are packaged.

Utility

The compounds of the present invention are useful for the control of undesired vegetation. They can be used for the selective control of weeds in crops, such as cotton, soybeans and sugarbeets, or wherever general weed control is required, such as on industrial sites, railroad rights-of-way and locations adjacent to croplands.

The precise amount of the compounds of the present invention to be used in any given situation will vary according to the particular end result desired, the use involved, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.1 to about 15 kilograms per hectare. The lower rates in this range will generally be selected for selective weed control in crops, on lighter soils, soils low in organic matter content, or in situations where maximum persistance is not necessary. In many situations it is advantageous to incorporate these chemicals with the soil.

The compounds of the present invention may be combined with any other herbicide and they are particularly useful in combination with herbicides of the substituted urea, uracil, triazone or s-triazine types for controlling a broad spectrum of weeds.

The following herbicidal compounds may be used in combination with the compounds of the instant invention:

5-amino-4-chloro-2-phenyl-3(2H)-pyridazinone (Pyrazon)
2-chloro-4,6-bis(ethylamino)-s-triazine (Simazine)
2-chloro-4-(ethylamino)-6-(isopropylamino)-s-triazine (Atrazine)
2-chloro-4,6-bis(isopropylamino)-s-triazine (Propazine)
2-[[4-chloro-6-(ethylamino)-s-triazin-2-yl]amino]-2-methylproprionitrile (Cyanazine)
4-amino-6-(1,1-dimethylethyl)-3-(methylthio)-1,2,4-triazin-5(4H)-one (Metribuzin)
3-(3,4-dichlorophenyl)-1,1-dimethylurea (Diuron)
3-[p-(p-chlorophenoxy)phenyl]-1,1-dimethylurea (Chloroxuron)
1,1-dimethyl-3-($\alpha,\alpha,\alpha$-trifluoro-m-tolyl)urea (Fluormeturon)
3-(3,4-dichlorophenyl)-1-methoxy-1-methylurea (Linuron)
5-bromo-3-sec-butyl-6-methyluracil (Bromacil)
3-cyclohexyl-5,6-trimethyleneuracil (Lenacil)
2-chloro-1-(3-ethoxy-4-nitrophenoxy)-4-trifluoromethyl-benzene
3-isopropyl-(1H)-2,1,3-benzothiadiazin-4(3H)-one, 2,2-dioxide (Bentazone)
1,1'-dimethyl-4,4'-bipyridium ion (Paraquat)
2,4-dichlorophenoxy acetic acid and salts
5-[2-chloro-4-(trifluoromethyl)phenoxy]-2-nitrobenzoic acid, sodium salts (Blazer ®)

Herbicidal activity of the subject compounds was discovered in a number of greenhouse tests, as described below.

Test A

Seeds of crabgrass (*Digitaria* spp.), barnyardgrass (*Echinochloa crusgalli*), wild oats (*Avena fatua*), cassia (*Cassia tora*), morningglory (*Ipomoea hederacea*), cocklebur (*Xanthium* spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bushbeans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

Ratings for compounds tested by this procedure are recorded in Table A. The ratings are based on a numerical scale extending from 0=no injury, to 10=complete kill. The accompanying letters have the following meanings: C=chlorosis/necrosis, B=burn, G=growth retardation, E=emergence inhibition, H=formative effect, and X=axillary stimulation.

TABLE A

| | $(C_2H_5O)_2\overset{O}{\underset{\|}{P}}CCl_2CO_2-$ | $(CH_3CH_2O)_2\overset{O}{\underset{\|}{P}}CCl_2CO_2-\overset{CH_3}{\underset{S}{\bigcirc}}$ | | $(nC_4H_9O)_2\overset{O}{\underset{\|}{P}}CCl_2CO_2-$ | |
|---|---|---|---|---|---|
| kg/ha | 0.4 | 0.4 | 2 | 0.4 | 2 |
| POST EMERGENCE | | | | | |
| BUSH BEAN | 0 | 0 | 0 | 0 | 1B |
| COTTON | 0 | 0 | 2H | 0 | 1B 2H |
| MORNING GLORY | 0 | 0 | 3H | 0 | 2H |
| COCKLEBUR | 0 | 0 | 2G | 0 | 0 |
| CASSIA | 0 | 0 | 0 | 0 | 4G |
| NUTSEDGE | 2G | 0 | 0 | 0 | 0 |
| CRABGRASS | 8H | 5G | 9G | 6G | 1C 9G |
| BARNYARD GRASS | 7H | 1G | 8H | 1H | 1C 7H |
| WILD OATS | 0 | 0 | 0 | 0 | 0 |
| WHEAT | 0 | 0 | 0 | 0 | 0 |
| CORN | 6H | 0 | 0 | 0 | 1B 5H |
| SOYBEAN | 0 | 0 | 0 | 1H | 3H |
| RICE | 0 | 0 | 0 | 0 | 2G |

TABLE A-continued

| | | | | | |
|---|---|---|---|---|---|
| SORGHUM | 0 | 0 | 0 | 0 | 1B 3G |
| PRE EMERGENCE | | | | | |
| MORNING GLORY | 0 | 0 | 0 | 0 | 0 |
| COCKLEBUR | 0 | 0 | 0 | 0 | 0 |
| CASSIA | 0 | 0 | 0 | 3G | 0 |
| NUTSEDGE | 7G | 0 | 0 | 0 | 0 |
| CRABGRASS | 9H | 9H | 9H | 5H | 10H |
| BARNYARD GRASS | 10H | 9H | 9H | 7H | 9H |
| WILD OATS | 8G | 0 | 1H | 0 | 8H |
| WHEAT | 9H | 0 | 6G | 0 | 9H |
| CORN | 9H | 0 | 7H | 5G | 7H |
| SOYBEAN | 0 | 0 | 0 | 0 | 0 |
| RICE | 10E | 0 | 2G | 0 | 1G |
| SORGHUM | 10H | 5G | 8H | 3G | 7H |

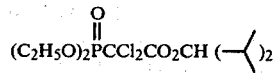
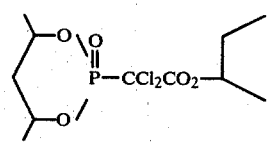

| kg/ha | 0.4 | 2 | 10 | 0.4 | 2 |
|---|---|---|---|---|---|
| POST EMERGENCE | | | | | |
| BUSH BEAN | 0 | 0 | 7B | | |
| COTTON | 0 | 0 | 4B | 0 | 2B 6G |
| MORNING GLORY | 0 | 1B | 10B | 0 | 0 |
| COCKLEBUR | 0 | 1B | 1B | 0 | 0 |
| CASSIA | 0 | 1B | 4B | 0 | 0 |
| NUTSEDGE | 0 | 0 | 0 | 0 | 5G |
| CRABGRASS | 0 | 0 | 1B 5H | 7H | 9G |
| BARNYARD GRASS | 0 | 1B | 4B | 8H | 8H |
| WILD OATS | 0 | 0 | 1B | 0 | 0 |
| WHEAT | 0 | 0 | 1B | 0 | 0 |
| CORN | 0 | 1B | 1B | 0 | 4G |
| SOYBEAN | 0 | 1B | 1B | 0 | 2G |
| RICE | 0 | 0 | 1B | 0 | 5G |
| SORGHUM | 0 | 0 | 2B | 0 | 5G |
| PRE EMERGENCE | | | | | |
| MORNING GLORY | 0 | 0 | | 0 | 1C |
| COCKLEBUR | 0 | | 0 | 0 | 3H |
| CASSIA | 0 | 0 | 0 | 1C | 5G |
| NUTSEDGE | 0 | 0 | 0 | 9G | 10E |
| CRABGRASS | 0 | 0 | 9H | 9H | 10H |
| BARNYARD GRASS | 0 | 0 | 9H | 10H | 10H |
| WILD OATS | 0 | 0 | 2H | 9H | 9H |
| WHEAT | 0 | 0 | 0 | 9H | 10E |
| CORN | 0 | 0 | 0 | 7H | 9H |
| SOYBEAN | 0 | 0 | 0 | 3G | 1H |
| RICE | 0 | 0 | 0 | 9H | 10E |
| SORGHUM | 0 | 0 | 9H | 9H | 10H |

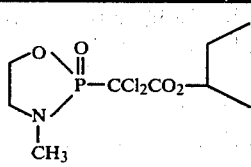
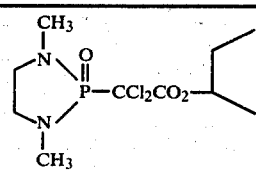
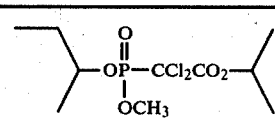

| kg/ha | 0.4 | 2 | 0.4 | 2 | 0.4 |
|---|---|---|---|---|---|
| POST EMERGENCE | | | | | |
| BUSH BEAN | 0 | 1H | 0 | 0 | 0 |
| COTTON | 0 | 0 | 0 | 0 | 1H |
| MORNING GLORY | 1H | 4H | 0 | 0 | 0 |
| COCKLEBUR | 0 | 0 | 0 | 0 | 0 |
| CASSIA | 1H | 0 | 0 | 0 | 2G |
| NUTSEDGE | 0 | 1H | 0 | 0 | 0 |
| CRABGRASS | 9G | 9G | 0 | 2H 5G | 9G |
| BARNYARD GRASS | 8H | 9H | 0 | 5H | 8H |
| WILD OATS | 0 | 0 | 0 | 0 | 0 |
| WHEAT | 0 | 0 | 0 | 0 | 0 |
| CORN | 0 | 0 | 0 | 2H | 0 |
| SOYBEAN | 0 | 2H | 1H | 5H | 1H |
| RICE | 0 | 5G | 0 | 0 | 0 |
| SORGHUM | 0 | 0 | 0 | 0 | 0 |
| PRE EMERGENCE | | | | | |
| MORNING GLORY | 0 | 3H | 0 | 0 | 0 |
| COCKLEBUR | 0 | 0 | 0 | 0 | |
| CASSIA | 0 | 0 | 0 | 0 | 0 |
| NUTSEDGE | 0 | 0 | 0 | 3H | 10E |

TABLE A-continued

| | | | | | |
|---|---|---|---|---|---|
| CRABGRASS | 8H | 9H | 5H | 9H | 9H |
| BARNYARD GRASS | 6H | 9H | 1H | 9H | 9H |
| WILD OATS | 0 | 6H | 0 | 1H | 8H |
| WHEAT | 0 | 9H | 0 | 1H | 9H |
| CORN | 0 | 1H | 0 | 1H | 8H |
| SOYBEAN | 0 | 3G | 0 | 3G | 1H |
| RICE | 5G | 10E | 0 | 2G | 9G |
| SORGHUM | 5H | 9H | 0 | 2G | 9H |

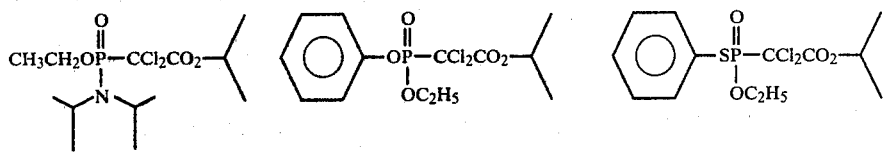

| kg/ha | 2 | 0.4 | 2 | 0.4 | 2 |
|---|---|---|---|---|---|
| POST EMERGENCE | | | | | |
| BUSH BEAN | | | 0 | 1B | 0 | 1B |
| COTTON | 3B | | 0 | 1H 3B | 0 | 2B,4G |
| MORNING GLORY | 2B | | 0 | 1B | 0 | 1B 4G |
| COCKLEBUR | 1B | | 0 | 0 | 0 | 0 |
| CASSIA | 1B | | 1H | 0 | 0 | 3G |
| NUTSEDGE | 1H | | 0 | 3G | 0 | 0 |
| CRABGRASS | 7H | | 9H | 9H | 8G | 1B 9H |
| BARNYARD GRASS | 3H | | 7H | 9H | 6H | 1B 9H |
| WILD OATS | 0 | | 0 | 8H | 0 | 1B 6H |
| WHEAT | 0 | | 0 | 0 | 0 | 1B |
| CORN | 0 | | 0 | 9H | 0 | 1B 2H |
| SOYBEAN | 2H 7G 5X | | 0 | 1B 1H | 1H | 1B 2H |
| RICE | 3G | | 0 | 0 | 0 | 1B |
| SORGHUM | 2G | | 0 | 0 | 1B | 1B 7G |
| PRE EMERGENCE | | | | | |
| MORNING GLORY | 5G | | 0 | 1H | 0 | 0 |
| COCKLEBUR | 0 | | 0 | 0 | 0 | 0 |
| CASSIA | 0 | | 0 | 2H | 0 | 0 |
| NUTSEDGE | 0 | | 0 | 7G | 5G | 5G |
| CRABGRASS | 9H | | 9B | 10E | 9H | 9H |
| BARNYARD GRASS | 9H | | 10H | 10H | 9H | 9H |
| WILD OATS | 1H | | 7G | 10H | 8H | 9H |
| WHEAT | 8H | | 4G | 10H | 2H | 8G |
| CORN | 9H | | 8H | 10H | 0 | 9H |
| SOYBEAN | 5H | | 0 | 4H | 2H | 6G |
| RICE | 2G | | 9H | 10E | 3G | 8G |
| SORGHUM | 7H | | 10H | 10H | 9H | 9H |

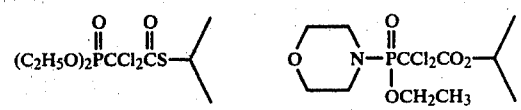

| kg/ha | 0.4 | 2 | .4 |
|---|---|---|---|
| POST EMERGENCE | | | |
| BUSH BEAN | 0 | 0 | 1H |
| COTTON | 0 | 0 | 2H |
| MORNING GLORY | 0 | 0 | 4H |
| COCKLEBUR | 0 | 0 | 0 |
| CASSIA | 0 | 0 | 3H |
| NUTSEDGE | 0 | 0 | 2G |
| CRABGRASS | 6G | 7G | 8G |
| BARNYARD GRASS | 3H | 9H | 5H |
| WILD OATS | 0 | 0 | 0 |
| WHEAT | 0 | 0 | 0 |
| CORN | 0 | 2G | 0 |
| SOYBEAN | 0 | 0 | 0 |
| RICE | 0 | 0 | 2G |
| SORGHUM | 0 | 0 | 0 |
| PRE EMERGENCE | | | |
| MORNING GLORY | 0 | 0 | 5H |
| COCKLEBUR | 0 | 0 | 0 |
| CASSIA | 0 | 0 | 3G |
| NUTSEDGE | 0 | 0 | 7G |
| CRABGRASS | 9H | 9H | 9H |
| BARNYARD GRASS | 9H | 5C 9H | 9H |
| WILD OATS | 0 | 3H | 2G |
| WHEAT | 0 | 0 | 10H |
| CORN | 0 | 4H | 9H |
| SOYBEAN | 0 | 2G | 7H |
| RICE | 0 | 10E | 9H |
| SORGHUM | 0 | 6H | 9H |

TABLE A-continued

| | $(CH_3OCH_2CH_2O)_2-\overset{\overset{O}{\uparrow}}{P}-CCl_2CO_2-\diagup$ | $(CH_3OCH_2CH_2O)_{\overline{3}}\overset{\overset{O}{\uparrow}}{P}CCl_2CO_2-\diagup$ |
|---|---|---|
| kg/ha | .4 | .4 |
| POST EMERGENCE | | |
| BUSH BEAN | | — |
| COTTON | | 0 |
| MORNING GLORY | | 1H |
| COCKLEBUR | | 0 |
| CASSIA | | 1H |
| NUTSEDGE | | 0 |
| CRABGRASS | | 5G |
| BARNYARD GRASS | | |
| WILD OATS | | 0 |
| WHEAT | | 0 |
| CORN | | 0 |
| SOYBEAN | | 1H |
| RICE | | 0 |
| SORGHUM | | 0 |
| PRE EMERGENCE | | |
| MORNING GLORY | 0 | 3H |
| COCKLEBUR | 0 | — |
| CASSIA | 2H | 3H |
| NUTSEDGE | 5G | 5G,1C |
| CRABGRASS | 8H | 9H |
| BARNYARD GRASS | 9H | 9H |
| WILD OATS | 4H | 7G |
| WHEAT | 9H | 9H |
| CORN | 9H | 9H |
| SOYBEAN | 5H | 8H |
| RICE | 7G | 6G |
| SORGHUM | 8H | 9H |

Test B

Two plastic bulb pans were filled with fertilized and limed Falsington silt loam soil. One pan was planted with corn, sorghum and several grassy weeds. The other pan was planted with soybeans, cotton, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), diallisgrass (*Paspalum dilatatum*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 5-inch diameter plastic pot was also filled with prepared soil and planted with rice and wheat. Another 5-inch pot was planted with sugarbeets. The above four containers were treated preemergence (compound sprayed on soil surface before seed germination).

Twenty-eight days after treatment, the plants were evaluated using the rating system as described for Test A. The data are summarized in Table B. The results show that the compounds are useful for the selective control of weeds in a number of crops, including soybeans and sugarbeets.

TABLE B

| Compound | $(C_2H_5O)_2\overset{\overset{O}{\|}}{P}CCl_2CO_2-\diagup$ | | | | | |
|---|---|---|---|---|---|---|
| Rate, kg/ha | 1/8 | 1/8 | 1/4 | 1/2 | 1 | 1 |
| Crabgrass | 10H | 9H | 10H | 10H | 10H | 10H |
| Barnyardgrass | 8H | 8H | 10H | 10H | 10H | 10H |
| Sorghum | 0 | 0 | 5H | 7H | 10H | 10H |
| Wild Oats | 2H | 0 | 6H | 8H | 9H | 10H |
| Johnsongrass | 2H | 4H | 4H | 10H | 10H | 10H |
| Dallisgrass | 3H | 7H | 8H | 10H | 10H | 10H |
| Giant Foxtail | 6H | 10H | 10H | 10H | 10H | 10H |
| Ky. Bluegrass | 4H | 5H | 10H | 10E | 10H | 10E |
| Cheatgrass | 0 | 0 | 8H | 9H | 10H | 10E |
| Sugarbeets | 0 | 0 | 0 | — | 0 | 6G |
| Corn | 0 | 0 | 6H | 7H | 9H | 6H |
| Mustard | 0 | 0 | 0 | 0 | 0 | 0 |
| Cocklebur | 0 | 0 | 0 | 0 | 0 | 0 |
| Pigweed | 0 | — | 0 | 0 | 5G | 3G |
| Nutsedge | 0 | 0 | 0 | 0 | 3G | 5G |
| Cotton | — | — | — | — | — | — |
| Morningglory | 0 | 0 | 0 | 0 | 0 | 2H |

TABLE B-continued

| | | | | | | |
|---|---|---|---|---|---|---|
| Cassia | 0 | — | 0 | 0 | 0 | — |
| Teaweed | 0 | — | — | — | — | — |
| Velvetleaf | 0 | 0 | 0 | 0 | 0 | 0 |
| Jimsonweed | 0 | 0 | 0 | 0 | 0 | 0 |
| Soybean | 0 | 0 | 0 | 0 | 2G | 3G |
| Rice | 0 | 4G | 0 | 8H | 7H | 5H |
| Wheat | 0 | 0 | 0 | 7H | 0 | 5H |

Compound 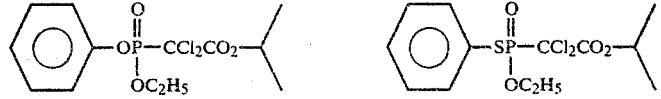

| Rate, kg/ha | 1/16 | 1/8 | 1/2 | 1/4 | 1 |
|---|---|---|---|---|---|
| Crabgrass | 0 | 4G | 10C | 0 | 10H |
| Barnyardgrass | — | — | — | 0 | 7H |
| Sorghum | 0 | 0 | 3G | 0 | 0 |
| Wild Oats | 0 | 0 | 0 | 0 | 0 |
| Johnsongrass | 0 | 0 | — | 0 | 5H |
| Dallisgrass | 0 | 0 | 3G | 0 | 3H |
| Giant Foxtail | 0 | 0 | 3H 5G | 5G | 3H |
| Ky. Bluegrass | 0 | 0 | — | 9H | 8H |
| Cheatgrass | 0 | 0 | 3G | 0 | 0 |
| Sugarbeets | — | 0 | — | 0 | 0 |
| Corn | 0 | 0 | 0 | 0 | 0 |
| Mustard | — | — | — | 0 | 0 |
| Cocklebur | 0 | 0 | 0 | 0 | 0 |
| Pigweed | 0 | — | 13 | 0 | 8C |
| Nutsedge | 0 | 0 | 0 | 0 | 0 |
| Cotton | — | — | — | 3G | 6G |
| Morningglory | 0 | — | — | 0 | 0 |
| Cassia | — | — | — | — | — |
| Teaweed | — | — | — | 0 | 0 |
| Velvetleaf | 0 | 0 | 0 | 0 | 0 |
| Jimsonweed | — | — | — | 0 | 0 |
| Soybean | — | 0 | 0 | 0 | 0 |
| Rice | 0 | 0 | — | 0 | 3G |
| Wheat | 0 | 0 | 0 | 0 | 2G |

Test C

Plastic bulb pans containing fertilized Fallsington silt loam were planted to corn, soybeans and cotton, planting depth 2.5 cm. The covering 2.5 cm layer of soil had been uniformly infested with a mixture of seeds of the following weed species: crabgrass (*Digitaria sanguinalis*) barnyardgrass (*Echinochloa crusgalli*), giant foxtail (*Setaria faberii*), johnsongrass (*Sorghum halepense*), velvet leaf (*Abutilon theophrasti*), jimsonweed (*Datura stramonium*) and mustard (*Brassica arvensis*). Immediately after planting, the soil surfaces were treated with a solution in a non-phytotoxic solvent of the compound whose structure is shown in Table C. One group of pots served as pre-emergence treatments; a second group was used to simulate soil-incorporated treatments whereby the surface-applied chemical was promptly mixed with the top 2.5 cm layer of soil containing the weed seeds. All of the pots were then watered from overhead at the rate of approximately 4 mm of water in a period of 160 minutes. The treated pots and controls were held in a greenhouse and on the twenty-eighth day after treatment were visually rated using the same scale and symbols as described hereinbefore. The data are shown in Table C.

TABLE C

Compound $(C_2H_5O)_2POCl_2CO_2$— 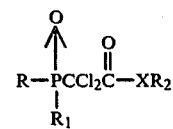

| Rate kg/ha | 1/32 | 1/16 | ¼ | ½ | 1 | — |
|---|---|---|---|---|---|---|
| *Pre-emergence* | | | | | | |
| WEEDS | | | | | | |
| Grasses | 0 | 0 | 3H | 3H | 8H | 0 |
| Broadleaves | 0 | 0 | 0 | 0 | 0 | 0 |
| CROPS | | | | | | |
| Corn | 0 | 0 | 0 | 0 | 0 | 0 |
| Soybeans | 0 | 0 | 0 | 0 | 3G | 0 |
| Cotton | 0 | 0 | 0 | 0 | 0 | 0 |
| *Soil-Incorporated* | | | | | | |
| WEEDS | | | | | | |
| Grasses | 0 | 0 | 3H | 4H | 8H | 0 |
| Broadleaves | 0 | 0 | 0 | 0 | 0 | 0 |
| CROPS | | | | | | |
| Corn | 0 | 0 | 0 | 0 | 5H | 0 |
| Soybean | 0 | 0 | 0 | 0 | 3G | 0 |
| Cotton | 0 | 0 | 0 | 0 | 0 | 0 |

What is claimed is:

1. A compound of the formula $$R-\overset{O}{\underset{R_1}{P}}Cl_2C-\overset{O}{C}-XR_2 \quad \text{II}$$

wherein
R is alkoxy of 1–6 carbons, alkoxy of 2–3 carbons substituted with alkoxy of 1–3 carbons, or —NR₃R₄ wherein
R₃ is hydrogen, alkyl of 1–4 carbons, cycloalkyl of 5–6 carbons, or

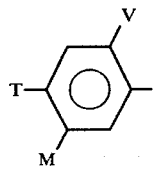

where
V is H, F, Cl, NO$_2$
T is H, F, Cl, Br, C$_1$–C$_3$ alkyl, CF$_3$
M is H, Cl, C$_1$–C$_3$ alkoxy, CF$_3$ provided M and T are not simultaneously CF$_3$;
R$_4$ is hydrogen, or alkyl of 1–4 carbons or methoxy provided that when R$_4$ is methoxy then R$_3$ is hydrogen or methyl;
[R$_3$ and R$_4$ may also be taken together to form a bridge having the structure $-(CH_2)_n-$ or $-(CH_2)_2-O-(CH_2)_2-$ or $-(CH_2)_2-N-(CH_2)_2-$
W where n is 4, 5, or 6 and W is hydrogen, methyl or ethyl.]

R$_1$ is alkoxy of 1–6 carbons, C$_2$–C$_3$ alkoxy substituted with an alkoxy of 1–3 carbons [or with 1–3 chlorines or with one bromine, alkenyloxy of 3–4 carbons,] or NR$_3$R$_4$;
[R and R$_1$ may be taken together to form a bridge of the structure $-O-(CH_2)_k-O-$, or $O-(CH_2)_k-N-$ or $-N-(CH_2)_k-N$
W                                      W X is oxygen; and
R$_2$ is 1-methylethyl or 1-methylpropyl;
provided that
(1) When R and R$_1$ are both 1-methylethoxy and X is oxygen, R$_2$ must not be 1-methylethyl;
(2) When R and R$_1$ are both methoxy or ethoxy and X is oxygen, R$_2$ must not be 1-methylethyl;
(3) When R and R$_1$ are both 1-methylpropoxy and X is oxygen, R$_2$ must not be 1-methylpropyl; and
(4) When R$_2$ is 1-methylethyl and one of R or R$_1$ is n-propyloxy then the other of R or R$_1$ cannot be n-butyloxy.

2. A compound of claim 1 wherein R is alkoxy of C$_1$–C$_3$ or C$_2$–C$_3$ alkoxy substituted with alkoxy of C$_1$–C$_3$.

3. A compound of claim 1, 1-methylpropyl-2,2-dichloro-2-(diethoxyphosphinyl)acetate.

4. A compound of claim 1, 1-methylethyl 2,2-dichloro-2[di-(1-methylpropoxy)phosphinyl]acetate.

5. A compound of claim 1, 1-methylpropyl 2,2-dichloro-2-[di-(1-methylethoxy)phosphinyl]acetate.

6. A compound of claim 1, 1-methylethyl 2,2-dichloro-2-[di-(n-propyloxy)phosphinyl]acetate.

7. A compound of claim 1, 1-methylethyl 2,2-dichloro-2-[diethylamino(ethoxy)phosphinyl]acetate.

8. A compound of claim 1, 1-methylethyl 2,2-dichloro-2-[ethoxy-(ethylamino)phosphinyl]acetate.

9. A compound of claim 1, 1-methylethyl 2,2-dichloro-2-[di-(2-methoxyethoxy)phosphinyl]acetate.

10. The compound 1-methylpropyl 2,2-dichloro-2-[ethoxyhydroxyphosphinyl]acetate, sodium salt.

* * * * *